(12) United States Patent
Liu et al.

(10) Patent No.: US 10,844,501 B2
(45) Date of Patent: Nov. 24, 2020

(54) CARBON SUPPORTED SINGLE ATOM CARBON DIOXIDE REDUCTION ELECTRO CATALYSTS

(71) Applicant: UCHICAGO ARGONNE, LLC, Chicago, IL (US)

(72) Inventors: Di-Jia Liu, Elmhurst, IL (US); Tao Xu, Naperville, IL (US); Dominic Rebollar, New Lenox, IL (US); Haiping Xu, Dekalb, IL (US)

(73) Assignees: UChicago Argonne, LLC, Chicago, IL (US); Board of Trustees of Northern Illinois University, DeKalb, IL (US)

( * ) Notice: Subject to any disclaimer, the term of this patent is extended or adjusted under 35 U.S.C. 154(b) by 45 days.

(21) Appl. No.: 15/915,259

(22) Filed: Mar. 8, 2018

(65) Prior Publication Data

US 2019/0276943 A1    Sep. 12, 2019

(51) Int. Cl.
| | | |
|---|---|---|
| C25B 11/04 | (2006.01) | |
| B01J 19/08 | (2006.01) | |
| C07C 1/12 | (2006.01) | |
| C07C 29/154 | (2006.01) | |
| C07C 29/158 | (2006.01) | |
| C07C 45/00 | (2006.01) | |
| C25B 3/04 | (2006.01) | |
| C25B 11/03 | (2006.01) | |
| C07C 51/00 | (2006.01) | |

(52) U.S. Cl.
CPC ......... *C25B 11/0478* (2013.01); *B01J 19/087* (2013.01); *C07C 1/12* (2013.01); *C07C 29/154* (2013.01); *C07C 29/158* (2013.01); *C07C 45/00* (2013.01); *C07C 51/00* (2013.01); *C25B 3/04* (2013.01); *C25B 11/035* (2013.01); *C25B 11/0405* (2013.01); *B01J 2219/0803* (2013.01); *B01J 2219/0875* (2013.01); *B01J 2219/0892* (2013.01)

(58) Field of Classification Search
CPC .................................. B01J 37/04; B01J 37/10
USPC .................................. 502/184, 185, 330, 344
See application file for complete search history.

(56) References Cited

U.S. PATENT DOCUMENTS

| | | | | |
|---|---|---|---|---|
| 3,625,768 A | * | 12/1971 | Moulton ................. | H01M 4/90 429/430 |
| 4,201,760 A | * | 5/1980 | Arendt ..................... | C01F 7/043 423/600 |
| 5,071,815 A | * | 12/1991 | Wallace ................... | B01J 23/02 502/302 |

(Continued)

FOREIGN PATENT DOCUMENTS

WO    2013/166505    * 11/2013    ............... G21F 9/00

OTHER PUBLICATIONS

Supplemental Information for "Synthesis of Supported Platinum Nanoparticles from Li—Pt Solid Solution," by Tao Xu et al. (Applicants submitted art). (Year: 2010).*

(Continued)

*Primary Examiner* — Patricia L. Hailey
(74) *Attorney, Agent, or Firm* — Foley & Lardner LLP

(57) ABSTRACT

Electrocatalysts composed of single atoms dispersed over porous carbon support were prepared by a lithium-melt method. The new catalysts demonstrated high selectivity, high Faradic efficiency and low overpotential toward to the electrocatalytic reduction of carbon dioxide to fuels.

20 Claims, 12 Drawing Sheets

(56) References Cited

U.S. PATENT DOCUMENTS

| | | | | |
|---|---|---|---|---|
| 2014/0291161 | A1* | 10/2014 | Awazu | C25C 3/34 |
| | | | | 205/348 |
| 2015/0311522 | A1* | 10/2015 | Fang | H01M 4/485 |
| | | | | 429/220 |
| 2019/0067706 | A1 | 2/2019 | Liu et al. | |
| 2019/0276943 | A1 | 9/2019 | Liu et al. | |

OTHER PUBLICATIONS

Jahangeer Ahmed et al., "Ultrafine Iridium Oxide Nanorods Synthesized by Molten Salt Method toward Electrocatalytic Oxygen and Hydrogen Evolution Reactions." Electrochimica Acta 212, pp. 686-693. (Year: 2016).*

Samuel J. Mugavero III, et al., "Materials discovery by crystal growth: Lanthanide metal containing oxides of the platinum group metals (Ru, Os, Ir, Rh, Pd, Pt) from molten alkali metal hydroxides." Journal of Solid State Chemistry 182, pp. 1950-1963. (Year: 2009).*

Abbasi, et al., "Tailoring the Edge Structure of Molybdenum Disulfide toward Electrocatalytic Reduction of Carbon Dioxide," ACS Nano 11(1), pp. 453-460 (2017).

Calvinho, et al., "Selective $CO_2$ reduction to C3 and C4 oxyhydrocarbons on nickel phosphides at overpotentials as low as 10 mV," Energy & Environmental Science 11, pp. 2550-2559 (2018).

Duan, et al., "Amorphizing of Cu Nanoparticles toward Highly Efficient and Robust Electrocatalyst for $CO_2$ Reduction to Liquid Fuels with High Faradaic Efficiencies," Advanced Materials 30(14), 1706194, 7 pages (2018).

Kim, et al., "Copper nanoparticle ensembles for selective electroreduction of $CO_2$ to C2—C3 products," Proceedings of the National Academy of Sciences 114(40), pp. 10560-10565 (2017).

Wang, et al., "$CO_2$ reduction to acetate in mixtures of ultrasmall $(Cu)_n,(Ag)_m$ bimetallic nanoparticles," Proceedings of the National Academy of Sciences 115(2), pp. 278-283 (2018).

Xu, et al., "Synthesis of Supported Platinum Nanoparticles from Li—Pt Solid Solution," Journal of the American Chemical Society 132(7), pp. 2151-2153 (2010).

Yang, et al., "Atomically dispersed Ni(I) as the active site for electrochemical $CO_2$ reduction," Nature Energy 3, pp. 140-147 (2018).

Barkholtz, et al., "Lithium Assisted 'Dissolution—Alloying' Synthesis of Nanoalloys from Individual Bulk Metals," Chemistry of Materials 28(7), pp. 2267-2277 (2016).

Lin, et al., "Direct Synthesis of Bimetallic $Pd_3Ag$ Nanoalloys from Bulk $Pd_3Ag$ Alloy," Inorganic Chemistry 51(24), pp. 13281-13288 (2012).

* cited by examiner

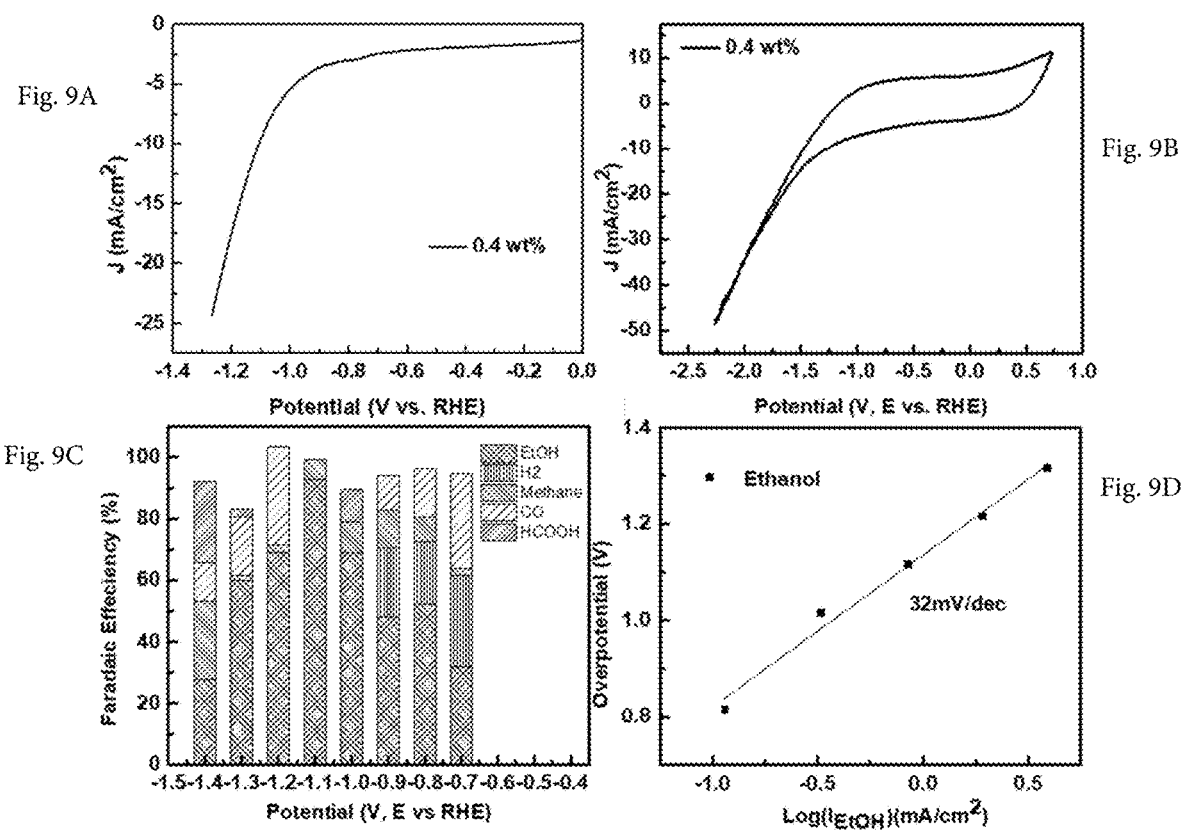

CARBON SUPPORTED SINGLE ATOM CARBON DIOXIDE REDUCTION ELECTRO CATALYSTS

The United States Government claims certain rights in this invention pursuant to Contract No. W-31-109-ENG-38 between the United States Government and the University of Chicago and/or pursuant to DE-AC02-06CH11357 between the United States Government and UChicago Argonne, LLC representing Argonne National Laboratory.

TECHNICAL FIELD

The present disclosure relates generally to methods and materials relating to electro-catalysts for $CO_2$ reduction.

BACKGROUND

Carbon dioxide emissions have been nearly continuously increasing since the dawn of the industrial revolution. These increases in carbon dioxide have become a concern as it is considered a contributor to the greenhouse gas, which has been associated with issues such as global warming. Thus, there is a desire to remove carbon dioxide from the environment or treat carbon dioxide at the source prior to release to the environmental. To electrochemically convert carbon dioxide to chemicals and fuels represents very attractive ways to address $CO_2$ emission, particularly when low-cost renewable energy sources, such as wind and solar, are available to use.

Conventional methods of converting $CO_2$ to fuels typically apply heterogeneous catalysis in gas phase at elevated temperature. For example, $CO_2$ can be catalytically converted to CO in the presence of hydrogen through the reverse water-gas shift reaction at a temperature above 200° C. $CO_2$ also can be catalyzed to form methanol over $Cu/ZnO/Al_2O_3$ in the presence of hydrogen under very high pressure (50-100 bar). Heterogeneous catalysis requires high temperature and high pressure, adding complexity and cost to the conversion system and manufacturing process. Furthermore, the chemical plant requires high footprint and energy consumption and is difficult to scale for small and mid-size operations. Ideally, carbon dioxide reduction systems should operate under low temperatures and low pressure to yield high amounts of product. Furthermore, it should be easy to scale-up to match the level of $CO_2$ conversion at different scales.

Electro-catalytic $CO_2$ reduction reaction (CRR) offers the benefit of converting carbon dioxide to fuels at ambient temperature and pressure in the aqueous phase, rendering it a desirable process. Such conversion, in general, can be facilitated in the presence of electro-catalysts. Typically, the electro-catalyst is composed of catalytically active sites supported by a conductive substrate, such as carbon. The catalytic reactions generally take place on the surface and inside of the pores of the catalyst material. The microporosity of the catalyst will also increase the carbon dioxide retention time inside of the porous carbon support, which could potentially alter the reaction pathways as well as products. Most importantly, the catalyst surface functionality and the nature of the catalytic active site play key roles in the catalytic activity and selectivity.

There have been reports of CRR catalysts that are consisting of either bulk materials, nanomaterials, or metal clusters. Some of the metals used in these catalysts as active centers are very expensive. For example, the most popular metal centers used are Ru, Pt, and Au, which are costly with very low natural reserves. The key shortcoming of such CRR catalysts is the lack of the scalability due to prohibitively expensive techniques or materials used for synthesis; therefore, these catalysts cannot be cost-effectively scaled to mass production as viable commercial products.

Another limitation of the current electro-catalyst technology is low selectivity and low efficiency as well as low stability. Furthermore, most current CRR catalysts can only convert $CO_2$ to $C_1$ molecules, such as CO, methane, formic acid, or methanol. For electro-catalytic conversion of $CO_2$ to fuel or chemicals, it is preferred that the conversion be highly selective under controlled conditions, such as voltage, so that product separation can be greatly simplified. The prior art catalysts do not have near to 100% selectivity toward one single product of higher $C_2$ products. The efficiency, or Faradaic efficiency, is equally important since it represents how effectively the electric charge is used to convert $CO_2$ to product instead of generating waste. The prior art catalysts do not have Faradaic efficiency near 100% in regards to $C_2$ products and above. The stability represents another important criteria for CRR electro-catalyst. Many prior art electro-catalysts lack stability due to dissolution of metals into the aqueous media. Furthermore, conversion of $CO_2$ to higher hydrocarbon compounds ($C_2$ or higher, such as ethanol) is more desired since the higher hydrocarbon compounds generally offer high heating value as fuel or as more valuable chemical intermediate. Prior art has not demonstrated CRR conversion to $C_2$ or higher products at close to 100% selectivity. All of these intrinsic failings of prior art catalysts still need to be overcome.

At present, there exist a limited number of single metal atom (SA) based catalysts. However; none of them has been utilized as the electro-catalysts for CRR. These SAs are typically synthesized using high-cost and low-yield methods, such as plasma coating, laser desorption, vapor deposition, as well as high temperature/high pressure processes. When such methods are used to apply metal atom over carbon, it has been found that agglomeration occurs, which leads to aggregated nanoparticles or an island of clusters. Therefore, the catalysts could not perform as true atomically dispersed catalysts for CRR.

Thus, there remains an: unmet need for CRR and for the formation of ethanol and hydrocarbons containing two or higher number of carbons for industrial applications.

SUMMARY

Embodiments described herein relate generally to electro-catalysts for carbon dioxide conversion, allowing for new routes to high energy density and high value hydrocarbon formation as well as high efficiency conversion of carbon dioxide. According to some embodiments, electro-catalysts containing atomically dispersed metal supported over high surface area carbon are prepared using a lithium-melt method. The metals are either in the form of monometallic single atoms or single atom "clouds." These electro-catalysts are demonstrated to be highly efficient with low overpotentials, highly selective toward the formation of hydrocarbons with $C_2$ or larger, and highly stable in promoting $CO_2$ to chemicals and fuels during electro-catalytic CRR. Specifically, the formation of ethanol and acetone at high selectivity and efficiency are observed, a highly sought after phenomenon in the field of $CO_2$ conversion.

One embodiment relates to a method of synthesizing a catalyst comprising: adding a catalytic metal in its metallic form to molten alkaline metal; atomically dispersing the catalytic metal in the molten alkaline metal; forming an alkaline metal-catalytic metal solid; converting a portion of the alkaline metal in the alkaline metal-catalytic metal solid to alkaline metal hydroxide forming a metal-alkaline metal hydroxide solid; mixing said metal-alkaline metal hydroxide solid with a conductive support material to form a mixture; removing alkaline metal hydroxide from the mixture leaving a mixture of atomically dispersed metal over the conductive support; and drying the mixture of atomically dispersed metal—the conductive support to produce the catalyst containing the catalytic metal atomically dispersed over the conductive support.

Another embodiment relates to a method of synthesizing a catalyst comprising: forming an dispersion of multiple metals in a molten alkaline metal; forming an alkaline metal-multiple metal solid; converting a portion of alkaline metal in the alkaline metal-first catalytic metal-second catalytic metal solid to an alkaline metal hydroxide forming an alkaline metal hydroxide-multiple metal solid; mixing said alkaline metal hydroxide-multiple metal solid with a conductive support material; removing alkaline metal hydroxide from the mixture of the alkaline metal hydroxide-multiple metal solid and a conductive support; and drying the multiple metal solid and conductive support mixture to produce the catalyst containing the multiple metals dispersed over the conductive support.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are, therefore, not to be considered limiting of its scope, the disclosure will be described with additional specificity and detail through use of the accompanying drawings.

FIG. 2A details a queue of non-bonded Cu single atoms marked by yellow circles. The line-scan intensity profile of FIG. 2B shows the existence of isolated Cu atoms with FWHM of ~1.38 Å, very close to the reported radius of a Cu atom (1.28 Å). FIG. 2C shows the Cu loading was 0.8 wt. % (0.8 wt. % Cu-on-C), highly dispersed Cu single atoms as well as some clusters of few Cu atoms, collected on the ultra-thin carbon film-covered gold TEM grid. FIG. 2C also shows that the clusters marked by yellow circles composed of loose and random ensembles of several to tens of Cu atoms with the interatomic distances longer than those observed in metallic Cu, which proved by the intensity profiles shown in FIG. 2D.

FIG. 6A 0.4 wt. % Cu-on-C; FIG. 6B 0.8 wt. % Cu-on-C; FIG. 6C 1.6 wt. % Cu-on-C. No large Cu cluster is observed.

FIG. 9A shows the linear scan voltammogram measured by rotating disk electrode in $CO_2$ saturated sodium bicarbonate solution (0.1M) against reference potential RHE over 0.4 wt. % Cu-on-C electrodes. FIG. 9B shows that the CV curve of 0.4 wt. % Cu-on-C electro-catalyst displayed obvious activity toward CRR in the potential range from 0V to −2.3V versus RHE. FIG. 9C shows the Faradaic efficiency and product distribution as a function of polarization potential using the 0.4 wt. % Cu-on-C electro-catalyst. At −1.1V, the FE and selectivity for ethanol can reach ~93%. FIG. 9D shows the Tafel slope plots for ethanol current density at various overpotentials. The Tafel slope of ethanol product is 32 mV/decade for 0.4 wt. % Cu-on-C electro-catalyst.

Figure 1:
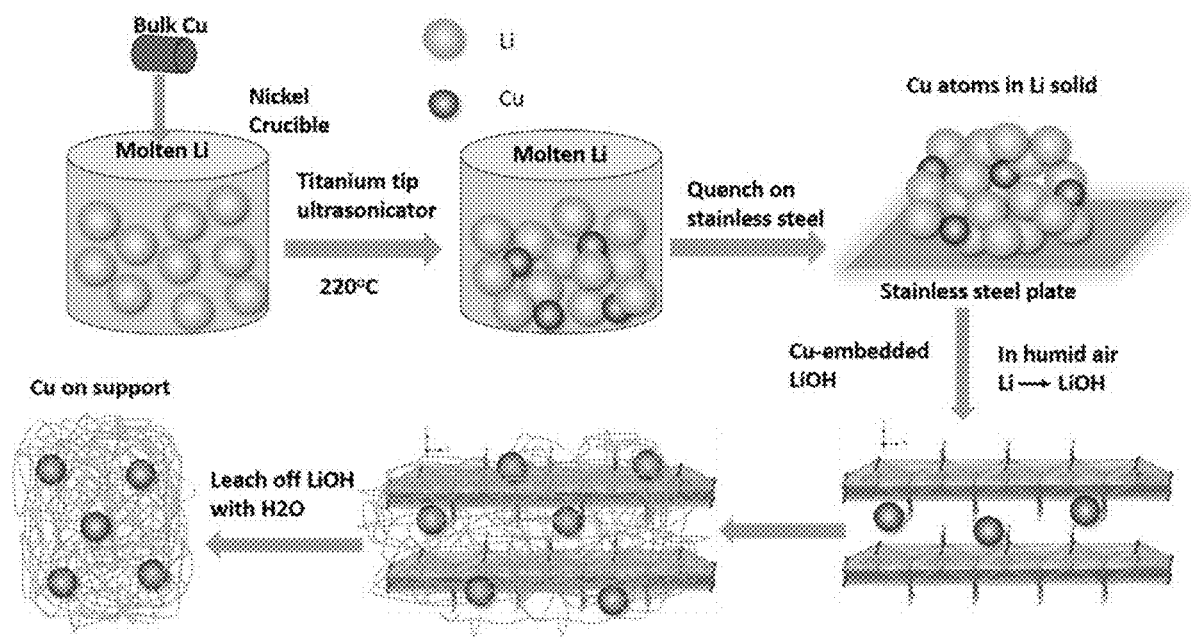
FIG. 1 illustrates one embodiment for a scheme for a synthesis process of Cu single atoms/clusters.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Certain embodiments described herein relate generally to single atom electro-catalysts and methods for synthesizing carbon supported single atom electro-catalysts using lithium melt method. Such a set of electro-catalysts can be used as catalysts for carbon dioxide reduction reactions (CRR), and towards the formation of $C_1$ molecules such as carbon monoxide, formic acid, methanol, and more importantly, $C_n$ ($n \geq 2$) hydrocarbons from carbon dioxide. The catalysts, according to some embodiments, exhibit excellent selectivity, efficiency, and stability for converting carbon dioxide towards production of high order hydrocarbons under very low overpotentials.

A new class of CRR electro-catalyst is synthesized using bulk metal and high surface area carbonaceous support as raw materials. Electro-catalysts, according to one embodiment, are active even for low temperature aqueous application. These catalysts have a composition of stable and highly dispersed single atom metal (for example, a transition metal (TM)) decorated inside of carbonaceous material. As used herein, "decorated" refers to a uniformly distributed single atom system present throughout the carbonaceous material from the outside to the inside of the porous material.

In one embodiment, such CRR electro-catalysts are prepared in the following steps. First, bulk metal is dissolved into molten lithium to form metal solution in lithium and then quenched quickly in the moisture-free and oxygen-free environment. Second, the Li in the Li-metal solid solution is converted to solid LiOH in moist air, while keeping dissolved metal atoms segregated from each other by the solid LiOH. Third, the mixed metal-on-LiOH is mixed with conductive supports such as high surface carbon; catalysts can be collected on to the surface of non-water soluble support materials such as carbon when the LiOH was selective leached off with water under ambient condition with a yield of 90%. Finally, LiOH in water during the leaching step will oxidize the carbon surface to form functional groups, such as —OH, —COOH, —CO, etc., over the carbon surface. Such functional groups, in turn, help to anchor the single metal atoms (of the bulk metal) on the carbon support surface in a highly dispersed state. A schematic presentation of Li-melt-based electro-catalyst for CRR is shown in FIG. 1. Synthesis of single atoms is carried out in an inert atmosphere glovebox. Using a crucible, lithium is heated to above its melting point of 180.5° C. and kept below its boiling point of 1330° C., to which a relative amount of Cu is added. An ultrasonic homogenizer is used to ensure a uniform dispersion of metal single atoms while the lithium melt is maintained for between 1 and 4 hours. Formation of a solid solution is achieved by rapidly pouring the melt onto a clean stainless-steel plate to quench the melt and avoid aggregation of metal components. In one embodiment, the molten material is cooled in less than 1 min, such as about 30 s. Once the Li—Cu melt solid cools, the solid solution is removed from the glovebox and cut into small pieces. The solid solution pieces are slowly converted from Li to LiOH using humidified air. The ensuing Cu single atoms/clusters/LiOH materials are combined with the designated amount of carbon support and thoroughly mixed with a mortar and pestle until the mixture is homogeneous. The LiOH is leached out with copious amounts of double-distilled water, leaving the Cu single atoms/clusters embedded in the amorphous carbon support. The resulting powder is collected and used to make an ink. The conversion of metallic lithium to LiOH is essential for the following rinsing step in water. The LiOH is easily soluble in water and, therefore, is thoroughly removed after the rinsing step.

In one embodiment, in the first step, one or more metals is dispersed in a heated alkaline metal melt. In one embodiment, alkaline metals, such as Li, Na, K, etc., can be used as the molten media to dissolve the aforementioned metals to form a solid solution. In a preferred embodiment, Li is used as the molten medium since it has the largest span between its melting point and boiling point.

The one or more metals added to the melt (generally referenced as the Li melt) are the metals ultimately provided as single atoms for the catalytic material. According to one embodiment, the metals applicable to the electro-catalyst preparation in this manner include Pt, Pd, Au, Ag, Ir, Ru, Rh, Cu, Zn, Cd, Hg, Sc, Y, Lu, Ti, Zr, Hf, V, Nb, Ta, Cr, Mo, W, Mn, Re, Fe, Co, Ni. In a preferred embodiment, the metals used for electro-catalyst preparation include those that can form solid solution in melting lithium less than 300° C., such as Pt, Pd, Au, Ag, Ir, Ru, Rh, Cu, Zn, Cd, Hg, Sc, Y, Lu. In a further preferred embodiment, Cu is used to convert $CO_2$ to ethanol and Rh is used to convert $CO_2$ to acetone. In particular, metal single atoms can be formed directly from bulk metal in the form of ingot, wire, powder, shredded pieces, etc. rather than the conventional wet chemistry synthesis methods involving dissolving metal salt or metal complex in aqueous or organic solution, following multi-step impregnation, drying, reduction, etc. The synthesis proceeds through the dispersion of transition metal into a hot lithium solution under inert atmosphere, which the temperature for molten Li is in the range from 180° C. to 1330° C., which covers the temperature range between lithium melting point and boiling point. For other alkaline metals used for the melt, the temperature range is between their respective melting points and boiling points.

The second step proceeds through converting the lithium to lithium hydroxide and mixing atomically dispersed metal in LiOH with carbonaceous substrate; LiOH can be easily washed away with water. In one embodiment, the lithium melt (Li-dissolved metal solid solution) is quenched quickly in the glovebox to form the solid Li. In one embodiment, the solidified lithium-dissolved metal solid solution is cut into small pieces to facilitate the interaction with moisture and oxygen for conversion to LiOH. Optionally, other mechanical methods that can break down solid solutions into finer pieces to facilitate the interaction with moisture and air can also be used. The lithium-metal solid solution pieces obtained after the reduction in size will be exposed to humidified air so that all of the lithium can be converted to lithium oxide and lithium hydroxide. It should be understood that for other alkaline besides lithium, the same basic physical processing can be done to facilitate formation of the respective alkaline metal oxide. During such process, lithium metal will first be oxidized by the oxygen in air to form lithium oxide, which subsequently reacts with moisture ($H_2O$) to form LiOH. In a preferred embodiment, humidified air should have relative humidity (RH) of 50% to 100%.

After conversion of the solid metal solution to the metal-LiOH mixture, the composite becomes powdered mixture, which can be mixed with the carbonaceous support using agate mortar-and-pestle by hand or ball milling machine for thorough mixing. During the mixing, the metal initially dissolved in metallic lithium remains to be atomically segregated by LiOH solid and is dispersed uniformly onto the carbon surface. In a preferred embodiment, the mixture should be ground into the size of 100 mesh to 300 mesh. The metal-LiOH-carbon mixture will be subsequently rinsed with copious de-ionized water. Water rinsing serves two purposes: first, it leaches out LiOH, which is readily soluble in water; second, it creates a concentrated alkaline solution which is known to modify carbon surface by forming OH, COH, COOH, etc. functional groups. Such groups can subsequently serve as the binding sites of atomically dispersed metal so that they remain segregated over the carbon surface after LiOH is removed. The washed composite is then dried under vacuum oven to remove the moisture at 50-100° C. After such process, the atomically dispersed metal is now transferred over conductive carbon surface for the electrochemical reaction while remaining highly segregated.

In some embodiments, in addition to monometallic single atom catalysts, bimetallic (or multi-metallic) systems as CRR catalysts can also be prepared using the current invention. In one embodiment, bulk bimetallic materials, such as $Pd_3Ag$ foil, etc., are added into the molten alkalithium at 250° C. for 4 h. During heating, the surface of the liquid remains mirror-shiny at all times. Preferably, to ensure the uniformity, the liquid is further ultrasonicated with a homogenizer equipped with a titanium tip. Sonication helps the dispersion of the bulk alloy into nanoparticles and prevents particles from precipitation and reaggregation due to gravity in molten Li. The resultant melt with the multi-metallic contents is then further processed as described above. For example, in one method, the hot liquid is then quenched by quickly pouring it onto a clean stainless-steel plate to avoid segregation of components. The solid solution is cut into thin pieces and placed in a humid air with 50RH % to 100RH %. The resulting gray solid grains are then ground into fine powders with an agate mortar and pestle. The resulting powder is mixed with carbon or any other substrates, which is further ground by agate mortar and pestle. The ground mixtures are leached with a large excess of water to remove the water-soluble LiOH. The catalysts are dried under vacuum at 50-100° C.

In one embodiment, another kind of bimetallic (or multi-metallic) single atom-dispersed catalysts can also be synthesized. Such bimetallic catalysts are formed by adding two or multiple metal foils, such as Cu, Zn, Pd, Pt, Ag, Au, Sn, Al, etc., into molten lithium. The resultant melt with the multi-metal contents is then further processed as described above. For example, in one method a solid solution was achieved by rapidly quenching the molten solution onto a clean stainless-steel plate to quench the melt and avoid segregation of metal components. The result is Li-M1-M2 (M1=first metal, M2=second metal) or Li-multi-metals melt. The multi-metal solids are then cut into small pieces and slowly converted from Li to LiOH using humidified air. The ensuing M1-M2/LiOH or multi-metals/LiOH composites are combined with carbon or any other kinds of substrates and mixed with an agate mortar with pestle and ball mill until homogeneous. The LiOH can be leached out with copious amounts of de-ionized water leaving the bimetallic or multi-metallic imbedded in the amorphous carbon support. The catalysts are dried under vacuum at 50-100° C. Examples include TMs and non-transition metals based nano-alloy electro-catalysts.

Following single atom synthesis process, the third step involves mixing metal-on-LiOH with a high surface area carbon support. In some embodiments, the support has a surface area of greater than 200 $m^2/g$, such as within the range from 200 $m^2/g$ to 800 $m^2/g$. The carbon support can either be commercial support, such as Vulcan XC-72 or Ketjen Black, or synthesized based on high surface area materials, such as, but not limited to, carbons derived from metal-organic frameworks and porous organic polymers. Metal atoms can be dispersed uniform on carbonaceous support with high specific surface area and high porosity within micropores. Using carbonaceous support generates electro-catalysts with high specific surface area and high porosity with micropore fraction. The metal atoms (single metal embodiments or multi-metal embodiments) over such supports are uniformly distributed to avoid or reduce agglomeration.

In addition, the catalysts can be easily processed into electro-catalyst inks for incorporation with traditional electrolyzer design. The catalysts have the following advantages: 1) showing activity and stability in aqueous media, 2) high selectivity as well as Faradaic efficiency achievable by controlling electrochemical potential, 3) easy application to surfaces as well as thin films or substrates, and 4) using low cost, earth-abundant transition metal and non-transition metal materials. All of these advantages are important for integration with electrolyzer. In addition, one embodiment is that the catalyst can be synthesized at benign processing condition using simple experimental setup at lower temperature in contrast to other single atom catalyst preparation, such as chemical vapor deposition, laser desorption, etc.

Figure 7A:
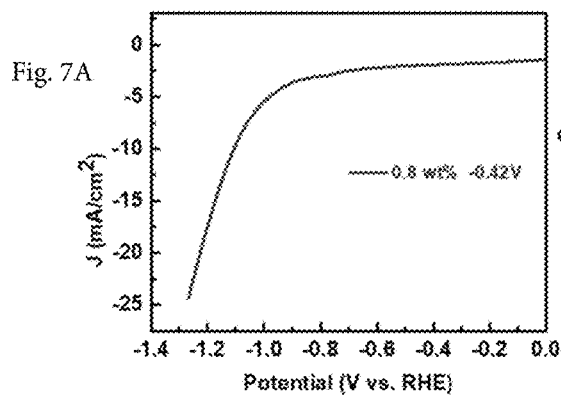
FIG. 7A shows the linear scan voltammogram measured by rotating disk electrode in $CO_2$ saturated sodium bicarbonate solution (0.1M) against reference potential of reversible hydrogen electrode (RHE) over 0.8 wt. % Cu-on-C electro-catalyst.
Figure 7B:
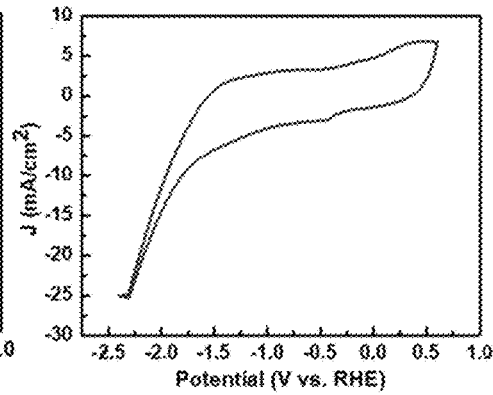
FIG. 7B shows that the cyclovoltammogram (CV) curve displayed obvious activity toward CRR in the potential range from 0V to −2.3V versus RHE.
Figure 7C:
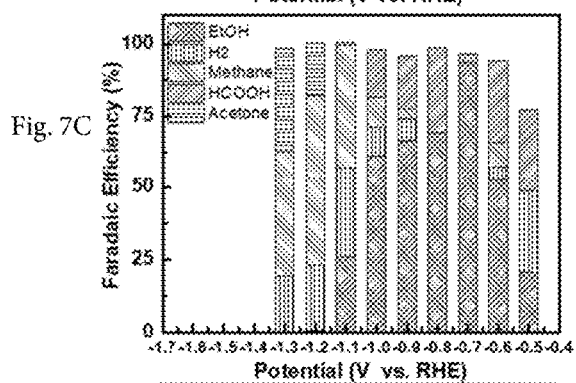
FIG. 7C shows the Faradaic efficiency and product distribution as a function of polarization potential using the 0.8 wt. % Cu-on-C electro-catalyst. At −0.7V, the FE and selectivity for ethanol can reach ~95% at −0.7V vs RHE.
Figures 11A, 11B:
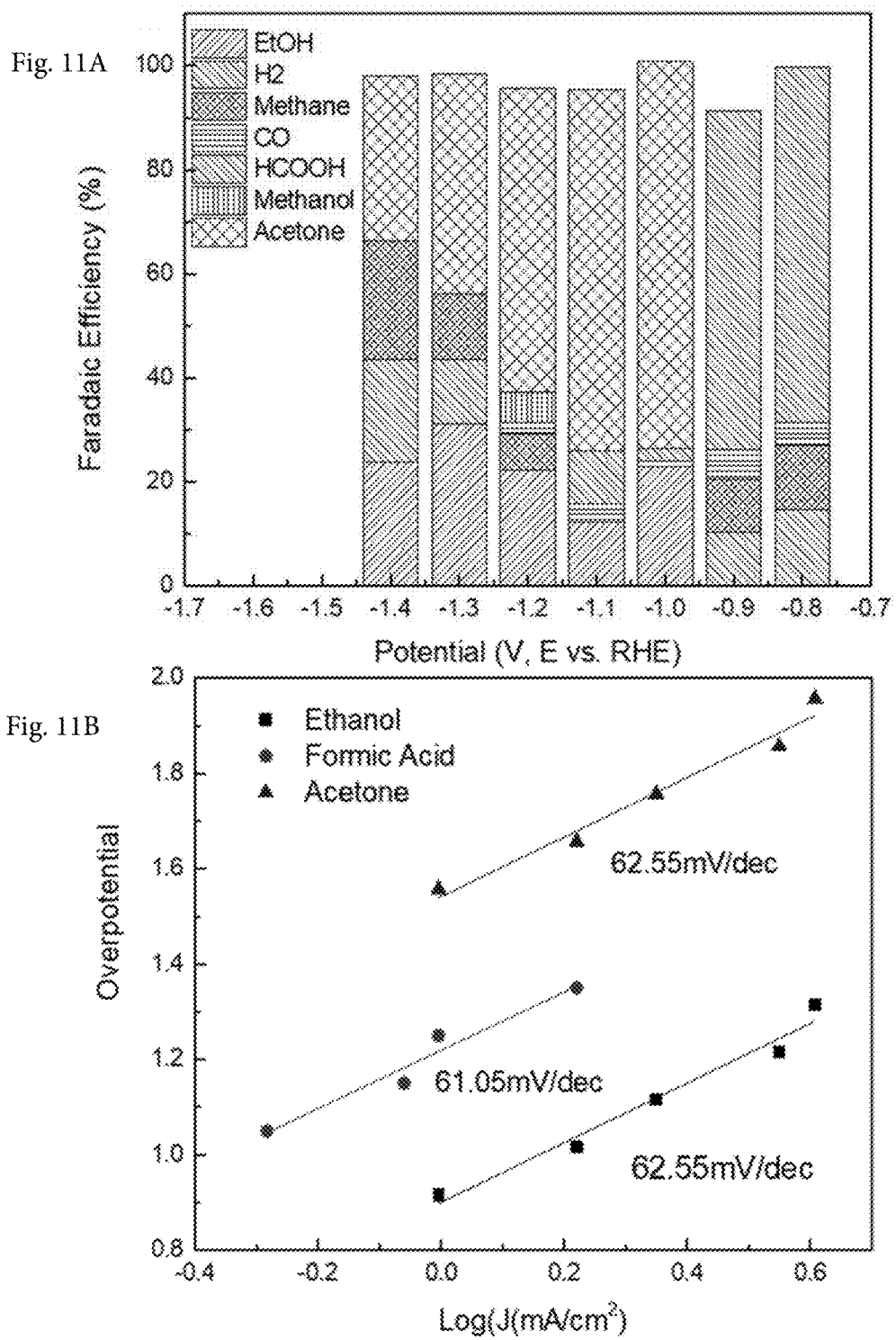
FIG. 11A shows the Faradaic efficient of 0.1 wt % Cu-on-C for different observed products versus applied potential.
FIG. 11B shows the Tafel plots for ethanol, formic acid and acetone production over 0.1 wt. % Cu-on-C.

Overcoming low product selectivity and low Faradaic efficiency of the existing electro-catalysts is a major challenge and is accomplished for embodiments described herein. The described CRR electro-catalysts, according to one embodiment, show high selectivity towards single product formation as well as high Faradaic efficiency. The selectivity approaches ~95% at electrode polarization potential of −0.7V (RHE) for 0.8 wt. % Cu-on-carbon FIG. 7C) and up to ~93% at −1.1V for 0.4 wt. % Cu-on-carbon (FIG. 9C). Cu are shown as completely isolated single atoms for 0.4 wt. % Cu-on-carbon and as a mixture of single atoms and clusters for 0.8 wt. % Cu-on-carbon. Compared to the literature and known arts where Cu is the form of metal crystallite or very large cluster, such high Faradaic efficiency and low polarization potentials is only observed over atomically dispersed Cu-on-carbon according to the current invention. Not limited by the theory, atomically dispersed Cu or Cu with very small cluster size, according to the current invention, are responsible for the high Faradaic efficiency and high product selectivity. This is in contrast to the literature reports where Cu based catalysts do not produce high selectivity and high CRR Faradaic efficiency simply because they are not in the atomically dispersed Cu or very small copper clusters, such as is described according to the current invention. The Faradaic efficiency for Cu based electro-catalyst, according to one embodiment, exhibits extremely high Faradaic efficiencies, approaching ~95%, resulting from highly dispersed metal over highly conductive high surface support with effective charge and mass transfers. This also elucidates that the Li melt process and post-treatment, such as LiOH leached off with water, creates highly dispersed metal anchored by oxygen modified carbon surface without degrading the conductivity of the support. As a result of high Faradaic efficiencies, the kinetics of the newly synthesized electro-catalysts are highly favorable. Ethanol was seen to be most favorable product, exhibiting a Tafel slope of 69.44 mV/decade. Meanwhile, a Tafel slope of 70.45 mV/decade was obtained for formic acid (FIG. 11B). The lower the Tafel slope, the faster overpotential decreases with the current density. Thus, the reaction exhibited low Tafel slope for ethanol product, indicating this electrochemical reaction can obtain a high current at low overpotential, which is favorable of the rate determining step of activating $CO_2$ molecules. Another important benefit of the electro-catalyst prepared herein, according one embodiment, is to control the product formation by simply adjusting the amount of metal loaded on carbon support. Yet another important benefit of the electro-catalyst prepared herein, according one embodiment, is to control the product formation by simply adjusting the CRR polarization potential applied to the catalyst.

The Faradaic efficiency for Cu based electro-catalyst, according to one embodiment, exhibits extremely high Faradaic efficiency towards acetone product, which is up to 70% for 0.1 wt % Cu-on-carbon (FIG. 11A).

Figure 12A:
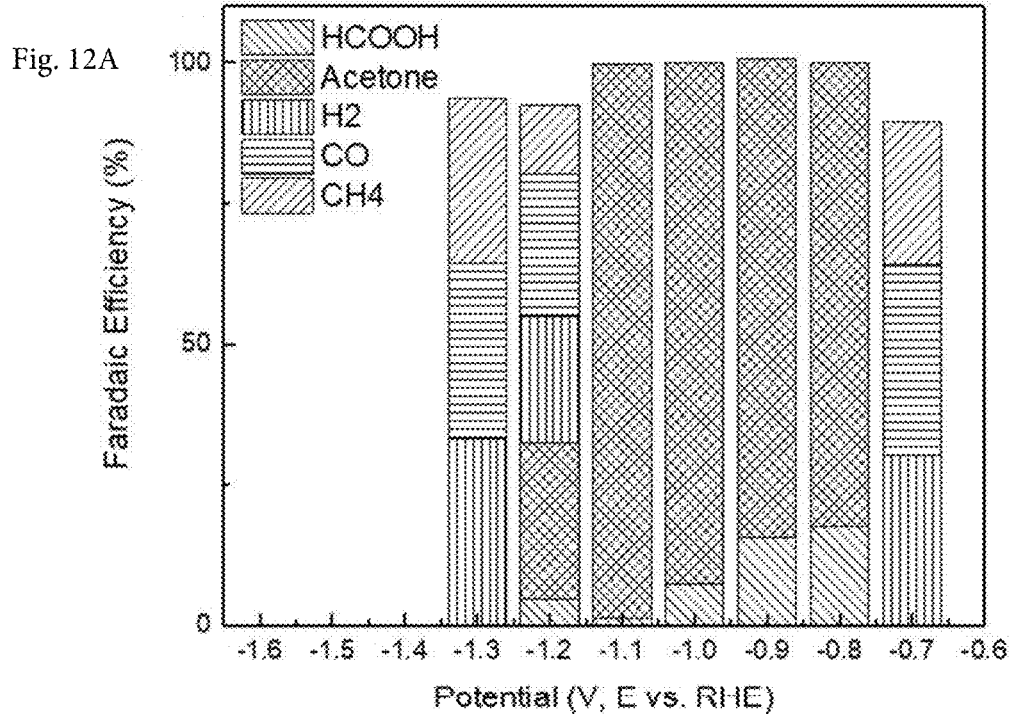
FIG. 12A shows the Faradaic efficient of 0.034 wt. % Rh-on-C for different observed products versus applied potential.
Figure 12B:
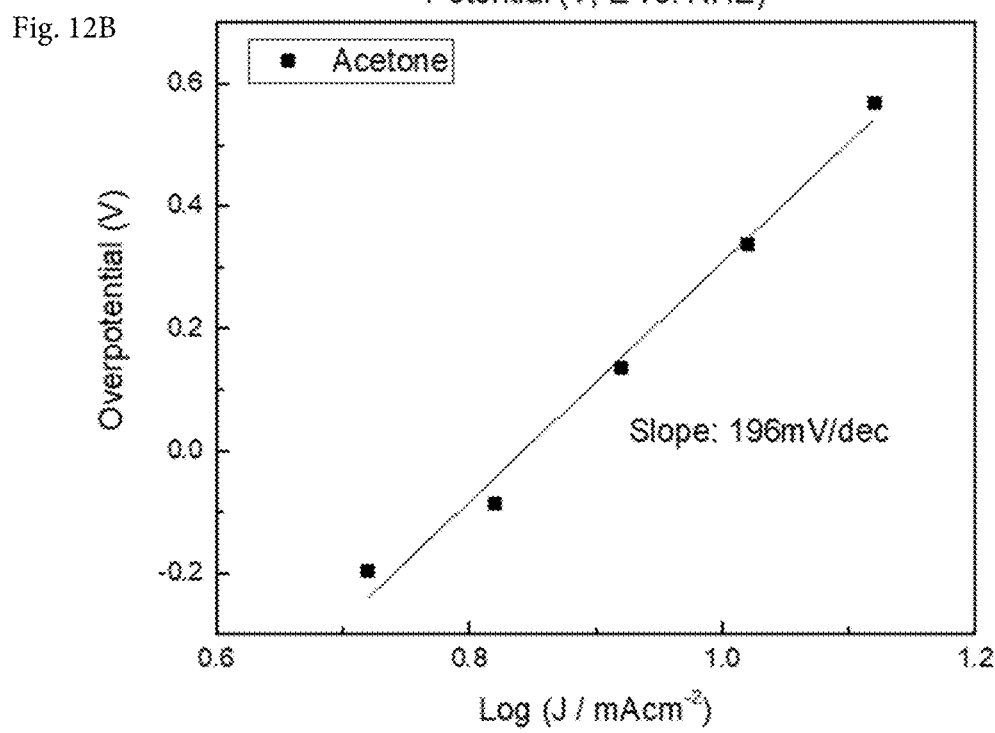
FIG. 12B shows the Tafel plots for acetone production over 0.034 wt. % Rh-on-C.

The Faradaic efficiency for Rh based electro-catalyst (Rh-on-C), according to one embodiment, exhibits extremely high Faradaic efficiency towards acetone product, which is higher than 97% for 0.034 wt. % Rh-on-carbon (FIG. 12A).

Unlike many prior art CRR catalyst synthesis which use metal salt wet chemistry, electroplated metal salts, plasma coated metals and metal oxides, or other deposition methods, herein the single atoms-/clusters-derived catalyst, according to one embodiment, uses Li-melt solution chemistry synthesis, which offers true single atom dispersion from the combination of single atom segregation by LiOH when applied to carbon support, alkaline solution-oxidized carbon surface for single atom anchoring and no high-temperature treatment after mixing with carbon. Furthermore, the preparation method can be easily scaled-up. The metal-on-carbon catalysts prepared according to embodiments described herein use commercial carbon supports, of which the application to porous substrates or electrode surfaces is well understood without the need for further alteration in processing techniques.

Electro-catalysts prepared as described herein have several advantages over that of prior art, including: 1) high Faradaic efficiency, 2) high selectivity for desired chemical species, 3) high aqueous stability, and 4) controllable product output by controlling operating potential as well as metal catalyst loading.

Electro-catalysts, in accordance with embodiments herein, exhibit high selectivity for the production of individual chemical species. Prior art research on Cu catalyst has shown low selectivity towards individual chemical species, lower than 60% for ethanol; whereas the electro-catalysts synthesized using Li solution method, according to one embodiment, shows nearly 95% selectivity toward ethanol formation and nearly 100% toward acetone formation, all well above previously reported electro-catalytic selectivity. For industrial application, high selectivity is crucial to reducing separation costs and product yield. Not limited by the theory, this high selectivity is present in part due to different catalytic mechanism over single atom site, in comparison with metal crystallites in the prior arts. Single metal site can produce the final products by unique sequential catalytic steps and synergistic catalytic steps with adjacent single atom sites, which offers better control in reaction mechanism than the metal crystallite catalyst offered by prior art. Further, the metal-support interactions may be fine-tuned through optimization of the metal loading and support surface modification.

Figures 10A, 10B:
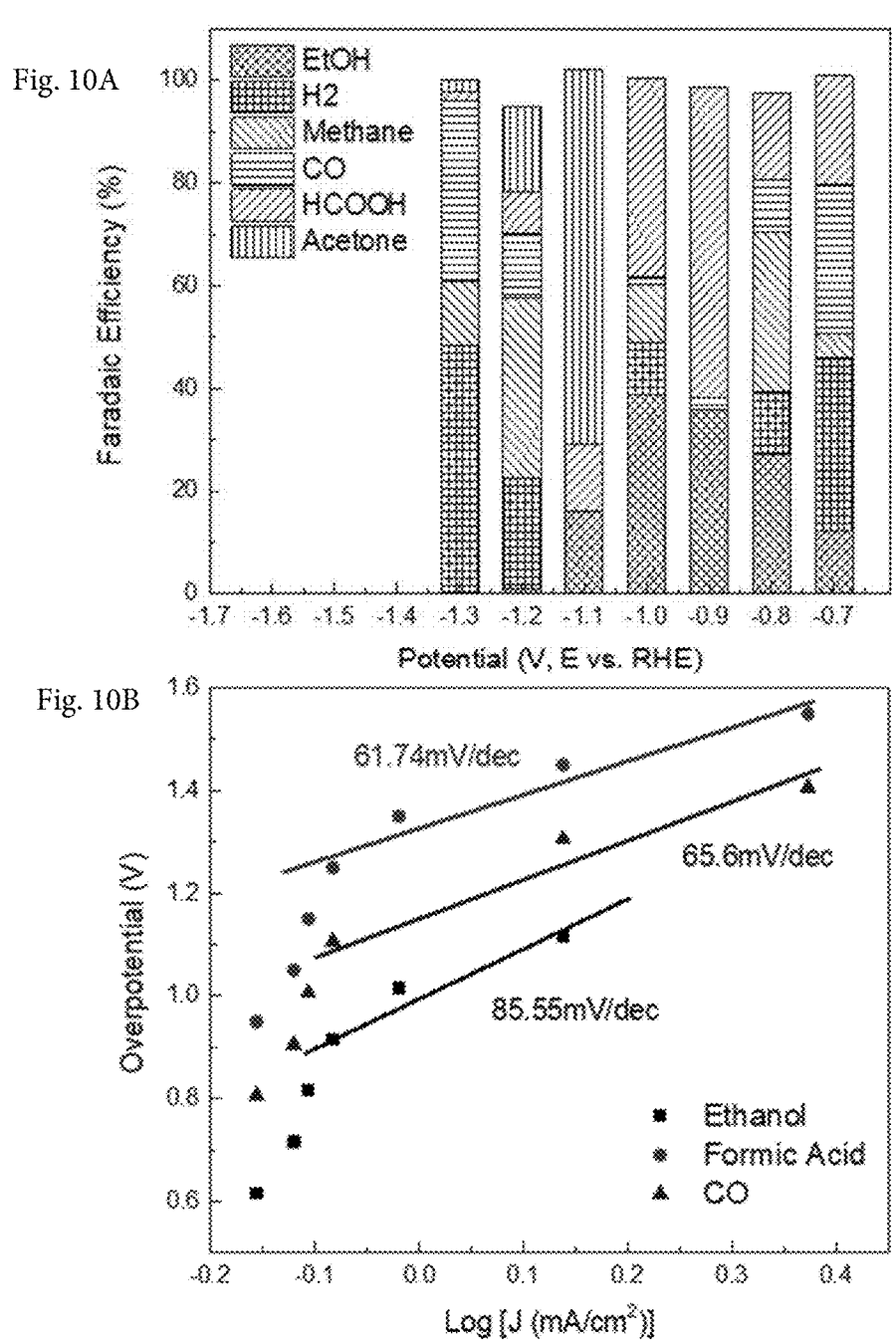
FIG. 10A shows the Faradaic efficient of 1.6 wt % Cu-on-C for different observed products versus applied potential.
FIG. 10B shows the Tafel plots for ethanol and formic acid production over 1.6 wt % Cu-on-C.

For one embodiment, 0.1 wt. % Cu-on-carbon, 0.4 wt. % Cu-on-carbon, and 0.8 wt. % Cu-on-carbon exhibit high selectivity and Faradaic efficiency for ethanol product, but other loadings, such as 1.6 wt. % Cu-on-carbon (FIG. 10A) or 6 wt. % Cu-on-carbon, exhibit mixed product formation with lowered Faradaic efficiency. This further demonstrates the importance of single atom dispersion in controlling catalytic mechanism since the higher metal loadings (1.6 wt. % and 6 wt. %) tend to lead to larger metal crystallite formation and, therefore, lower product selectivity due to existence of a variety of crystallite sizes. Importantly, the catalyst should contain higher metal loading while maintaining single atom dispersion. The balance between higher metal loading and higher metal dispersion represents an important embodiment of current invention.

Electro-catalysts in accordance with embodiments herein exhibit very high stability in aqueous media as well as under high overpotentials. As shown in FIG. 7F, this stability can reach and exceed 8 hours. The high surface area carbon support allows for increased stability as carbon does not easily degrade at low overpotentials. Most importantly, the preparation method according to the current invention produced a high level of oxygenated functional group, such as —OH, —COH, —COOH, during the rinsing of alkaline hydroxide, LiOH. Such oxygenated functional groups serve as anchoring sites to retain single metal atom in highly dispersed state during the catalytic reaction. Therefore, the catalysts demonstrate high stability. Such structural features are superior to the conventional CRR catalyst preparations in which no oxygenated functional groups were introduced. The metal in the catalysts prepared by the conventional methods will migrate and agglomerate during the catalytic reaction, leading to the change of catalytic activity due to the agglomeration of metal clusters.

The single atom, lithium solution method derived CRR electro-catalysts are different in composition, according to one embodiment, in that they are composed of well distributed single atoms. First, the catalyst composition of CRR catalysts contain the metals, such as Pt, Pd, Au, Ag, Ir, Ru, Rh, Cu, Zn, Cd, Hg, Sc, Y and Lu, Cu and Rh, being the most preferred. In prior art catalysts, copper is the most preferred metal in bulk or in nanomaterials but has never been shown in single atom form as exhibited here. Second, the single atoms in the CRR catalysts, according to the current invention, generally exhibit in their oxidized state, such as $Cu^{2+}$ or $Cu^{1+}$, as the result of binding with oxygenated functional groups in carbon support and exposure to oxygen in air. The apparent oxidative states result from the electron density redistribution from single metal atom to the oxygenated binder sites. Thus, the physical structure and the chemical state of the metal are different from that of other CRR catalysts which are dominated by metallic states, such as $Cu^0$.

FIG. 7F illustrates the long term stability of 0.8 wt. % Cu-on-carbon loading under −0.7V for 8 hours. The even current density attests to the stability of both the catalysts. Chronoamperogram testing shows high stability in aqueous media for copper single atom catalysts at high potentials. The catalyst retains stable current density and high Faradaic efficiency (more than 80% during the entire stability test).

Described herein are copper single atom-based catalysts for electro-catalytic $CO_2$ reduction to ethanol, acetone and other $C_1$ and $C_2$ hydrocarbons with key performance index well exceeding the current state of the art research. Rather than converting metal ions to metal nanoparticles or nanocrystallites in the inevitable presence of reducing agents and dispersing organic surfactants, bulk metal is directly dissolved into individual metal atoms in molten lithium and the disperse metal atoms is collected in the format of single atom onto a conductive carbon support by leaching out the lithium hydroxide with water. At the same time, the hydroxide solution modified the carbon surface with the oxygenated functional groups, which anchor the atomically dispersed metal through reactive binding and oxidation. As a result, and as supported in the examples below, the material described herein exhibits surprisingly improved results in critical metrics. For example, the FE of $CO_2$ reduction to ethanol on the Cu single atom-based catalysts strikingly reaches ~95% at low polarization potential of −0.7V vs RHE. The FE of $CO_2$ reduction to acetone on the Rh single atom-based catalysts reaches ~100%. In additional, the minimal overpotential can reach to −0.5V with FE of ~20%. The copper catalysts prepared by this method also exhibit extraordinary stability during electrochemical catalytic $CO_2$ reduction to ethanol for over 8 h with FE consistently above 80%.

The following examples are provided for illustrative purposes and should not be considered limiting as to the scope of the invention.

Example 1

Synthesis was carried out for a Li-melt-based electrocatalyst for CRR, as shown in FIG. 1. Synthesis of Cu single atoms/clusters were carried out in an Ar-filled glovebox, (oxygen level <0.3 ppm). Using a nickel crucible, 0.256 mol of lithium (99.9% Alfa-Aesar) was heated to 220° C., to which 0.079 mmol of Cu wire (99.9% Alfa-Aesar) was added. A tip ultrasonic homogenizer was used to ensure a homogeneous dispersion of metal single atoms/clusters while the lithium melt was maintained at 220° C. for 2 hours. During heating, the surface of the liquid remained mirror-shiny and homogenous throughout. Sonication aided in the dispersion of the bulk Cu wires into single atoms/clusters and prevents them from precipitation and re-aggregation or settling in molten Li. Formation of a solid solution was achieved by rapidly pouring the molt onto a clean 316 stainless steel plates to quench the melt and avoid segregation of metal components. Once the Li—Cu melt solid cooled, the solution was removed from the glovebox, cut into small pieces, and slowly converted from Li to LiOH using humidified air. The ensuing Cu single atoms/clusters/LiOH materials was combined with the desired amount of carbon black (Vulcan XC-72R) and mixed with an agate mortar and pestle until homogeneous. The LiOH was leached out with copious amounts of double-distilled water leaving the Cu single atoms/clusters imbedded in the amorphous carbon support. The samples were dried under vacuum at 60° C. for 24 h. Different mass loading of samples on carbon black were prepared: 0.1 wt. % Cu-on-carbon, 0.4 wt. % Cu-on-carbon, 0.8 wt. % Cu-on-carbon, and 1.6 wt. % Cu-on-carbon.

Electro-catalysts were deposited onto RRDE electrodes using 3 depositions of 5 uL aliquots of prepared ink. The ink was prepared by adding 5 mg of powdered catalyst to 50 mg of Nafion® (5% in alcohols, Sigma) and 200 mg of methanol (Sigma). Catalysts were allowed to dry for 10 minutes each after catalyst deposition before testing.

$CO_2$ reduction reaction rates and selectivity were measured using 0.149 mg of catalyst at room temperature and ambient pressure in 30 mL of $NaHCO_3$ in a 250 mL reactor. Cyclic voltammetry, chronoamperometry, as well as electrochemically active surface area (ECSA) measurements were taken using MSR Rotator from Pine instruments on a 0.19525 $cm^2$ glassy carbon electrode rotating at 1600 rpm. The electrolyte was purged with argon or $CO_2$ for 30 minutes prior to testing to remove air from the environment. The electrolyte was purged with $CO_2$ for 30 minutes to allow full saturation and development of a buffer solution at pH 6.8 with $NaHCO_3$. Aliquots of electrolyte (1.0 mL taken, 0.2 mL used) were taken after each chronoamperomic cycle and combined with 0.1 mL of DMF and 1.6 mL of $D_2O$ for NMR analysis. DMF was used as an internal standard. The resulting hydrocarbon peaks were integrated and compared to the 7.76 ppm 1H DMF peak. To keep the analysis quantitatively sound, integration of DMF peak was taken between 8.00 ppm and 7.55 ppm for all samples. No peak shifting was observed in regard to the 7.76 ppm DMF peak throughout the samples. DMF standard peak shift was accounted for due to $D_2O$ incorporation and was uniform throughout measurements. The potential of Ag/AgCl (WPI, 3M KCl) electrode was routinely checked against fresh Ag/AgCl (CHI, 1M KCl) and Hg/HgO (CHI, 1M NaOH), which yielded potential differences of −24±4 mV and 75±6 mV, respectively. All potentials measured are converted to RHE scale by V (vs. RHE)=V (vs. Ag/AgCl, 3M KCl)+0.210V+0.0591×pH.

Gas-chromatograph (GC) analysis was used to quantify the gas phase products from CRR reaction. It was performed on a HP 6890 Series GC system, by continuously purging the electrolyte system with $CO_2$ while performing chronoamperomic measurements. The $CO_2$ was used as a carrier gas to drive any gaseous products from the reduction of $CO_2$ to an attached 0.6 L Teldar® PLV gas sampling bag. The gas bag was then sealed and drawn from using 2 mL aliquots that were tested.

NMR analysis was used to quantify the yield of liquid samples from CRR, such as ethanol, formic acid and others, during controlled potential electrolysis. NMR spectra were recorded on Bruker NMR spectrometers (AVANCE-400). 1H NMR spectra were referenced to residual solvent signals. At the end of electrolysis periods, gaseous samples (0.8 ml) were drawn from the headspace by a gas-tight syringe (Vici) and injected into the GC (Varian 450-GC, pulsed discharge helium ionization detector (PDHID). Calibration curves for $H_2$ and CO were determined separately.

HRTEM and HAADF-STEM analyses were used to characterize Cu single atoms and catalyst morphology. The analyses were performed by JEOL 2100F field emission TEM operated at 200 kV at CNM Argonne National Lab. For the TEM experiments, 0.4 wt % Cu-on-C sample was dispersed into water and then sonicated for 0.5 hours. The solution was directly dropped onto ultrathin carbon film on holey carbon support film backed gold TEM grid and then dried at 60° C. To visualize single atom structure, STEM was performed using a probe-corrected JEOL JEMARM200CF equipped with a 200 kV cold-field emission gun. Images were obtained in either the H/LAADF. For STEM experiments, the catalyst samples for STEM analysis was prepared by dispersing as-prepared Cu/LiOH in water solution, which was sonicated for 0.5 hours. The ultrathin carbon film on holey carbon support film backed gold TEM grid was dipped in to solution and then dried at 60° C. STEM energy dispersive X-ray spectroscopy (EDX) analysis were carried out on an aberration-corrected JEOL ARM-200CF (scanning) transmission electron microscope equipped with an Oxford EDX XMAX80 system.

Powder X-ray diffraction (PXRD) measurements were carried out to characterize copper particle size. It was carried out on a Rigaku Miniflex diffractometer with Cu Kα radiation ($\lambda$=1.5406 Å). Samples were prepared by placing them on a silicon zero diffraction plate with amorphous carbon-based grease.

X-ray absorption measurements (XAS) involved X-ray absorption near edge structure (XANES) and extended x-ray absorption fine structure (EXAFS) spectroscopy was employed to probe the local environment around Cu atoms in prepared samples, which acquired at the 10-BM beamline and Sector Beamline 20 of the Materials Research Collaborative Access Team (MRCAT) at the Advanced Photon Source (APS), Argonne National Laboratory (ANL). XANES is used to determine the oxidation state and electronic transitions and fingerprint the element of interest. EXAFS is used for determination of local structure (i.e., interatomic distances, coordination numbers, and the types of neighboring atoms with few angstroms around the element of interest, which is Cu in this case).

TABLE 1

Data of linear combination fitting results from synchrotron XANES analysis

|  |  | Cu | CuO | Cu2O | R-factor | Chi-square |
|---|---|---|---|---|---|---|
| LCF | 0.4 wt % | 0 | 0.887 | 0.113 | 0.0260 | 0.0034 |
|  | 0.8 wt % | 0.011 | 0.847 | 0.142 | 0.0260 | 0.0034 |
|  | 1.6 wt % | 0.091 | 0.754 | 0.155 | 0.0278 | 0.0033 |

Electrochemical Measurements

Electro-catalytic surface area of Cu loaded on carbon supports were determined by measuring double layer capacitances. Cyclic voltammetry (CV) was performed in the same electrochemical cell as in bulk electrolyses with a Nafion proton exchange membrane and 0.1M $NaHCO_3$ electrolyte. Then, while keeping the solution still, potential of the working electrode was swept between 1 mV and 200 mV vs Ag/AgCl (1 M KCl) at various scan rates (mV/s). CVs were obtained for a potential range in which no Faradaic processes were occurring, and the geometric current density was plotted against the scan rate of the CV. The slope of the linear regression gives the capacitance. Surface areas were estimated from Randles-Sevcik equation. Randles-Sevcik equation is as follows, $$Ip = (2.69 \times 10^5) n^{3/2} A D^{1/2} v^{1/2} c$$

Ip: peak current
n: number of moles of electrons per mole of electroactive species
A: area of electrode (cm2)
D: diffusion coefficient (cm2/s) v: scan rate (V/s)
C: concentration (mol/cm3)

By plotting Ip versus $v^{1/2}$ and measuring the slope, area (A) can be estimated. To experimentally confirm the validity of this approach, test measurements were performed on glassy carbon electrodes and highly polished graphite plates (with other unpolished sections sealed from the electrolyte), and the areas estimated were in close match to their expected areas. The same procedure was followed for carbon paper with geometric area 1 $cm^2$ to estimate its roughness factor and real surface area.

The Faradaic efficiencies (FE) of each product produced were calculated from the amount of charge passed to produce each product divided by the total charge passed during the overall run (liquid). For the gas phase products such as $CH_4$, CO, or $H_2$, FE was calculated as below:

$$FE = \frac{2FVGP}{RTi} \times 100\%$$

V (vol %) is the volume concentration of $CH_4$ or $H_2$ in the exhaust gas from the electrochemical cell (GC data). G (mL $min^{-1}$ at room temperature and ambient pressure) is the gas flow rate. i (mA) is the steady-state cell current. P=1.01×$10_5$ Pa, T=273.15 K, F=96485 C $mol^{-1}$, R=8.314 J $mol^{-1}$ $K^{-1}$.

For liquid phase products, such as ethanol, formic acid, acetone, etc., NMR analysis was used to quantify the yield of liquid samples during controlled potential electrolysis, calibrated by the internal standard of chemical with known concentration. Typically, a 200 µl sample of the electrolyte was mixed with 100 µl of 10 mM DMF for use as internal standards in 1.6 ml $D_2O$ for NMR analysis. The ratio of the area of the products' peak areas to the DMF peak area were compared to standard curves to quantify the concentrations of the reaction products. Current or Faradaic efficiencies of each product produced were calculated from the amount of charge passed to produce each product divided by the total charge passed during the overall run (liquid). The peaks were quantified by integrating the area below it. The relative peak area can be calculated as follows:

$$\text{relative peak area ratio(ethanol)} = \frac{\text{triple peak area at 1.1 ppm (ethanol)}}{\text{single peak area at 2.8 ppm } (DMF)}$$

The concentration of liquid products was obtained using the calibration curves. Take the calculation of ethanol ($C_2H_5OH$) as an example; the calculation is based on calibrated NMR spectrum with the ratio $r_{ethanol}$=1.50 and the slope of calibration curve $k_{ethanol}$. Thus, the concentration of ethanol in the catholyte ($C_{ethanol}$) is:

$$C_{ethanol} = \frac{r_{ethanol}}{k_{ethanol}}$$

Hence, number of electrons $N_{ethanol}$, required to produce ethanol during the entire $CO_2$ electro-reduction reaction is:

$$N_{ethanol} = C_{ethanol} \times V \times N_A \times 12e$$

Where V=volume of catholyte. The number of electrons required to form 1 molecule of ethanol is 12. From the chronoamperogram, $Q_0$. Hence, the total number of electrons measured:

$$N_{total} = \frac{Q_0}{e}$$

Hence, the faradic efficiency of ethanol is:

$$FE = \frac{N_{ethanol}}{N_{total}} \times 100\%$$

The catalyst stability was measured by RDE using chronoamperomic method. An example is shown in FIG. 7F. The current density at constant voltage of −0.7 V was collected as the function of time up to 6000 seconds. At the same time, samples were collected at different time interval to measure the concentration of the products, from which the Faradaic efficiencies were calculated.

Tafel slope of the catalytic activity was derived from the current density measurement as the function of polarization potential using standard conversion method. Examples are given in FIGS. 7D, 9D, 10B, and 11B.

Figure 2A:
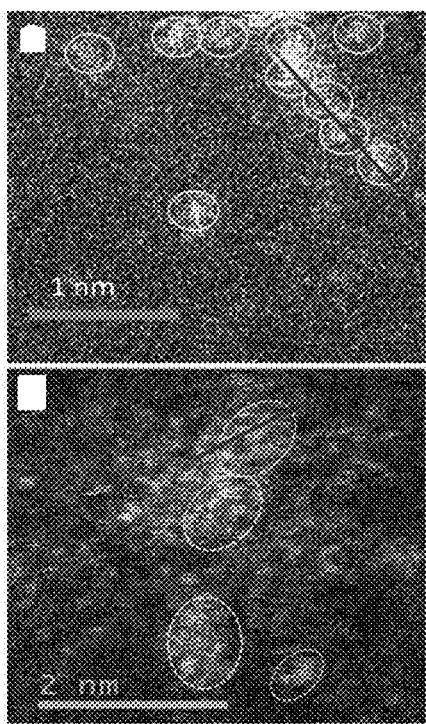
FIGS. 2A-2D show a representative HAADF-STEM image of all the Cu species existed exclusively as isolated single atom; neither clusters nor nanoparticles were detected when the Cu loading was 0.4 wt % (0.4 wt % Cu-on-C).
Figure 2B:
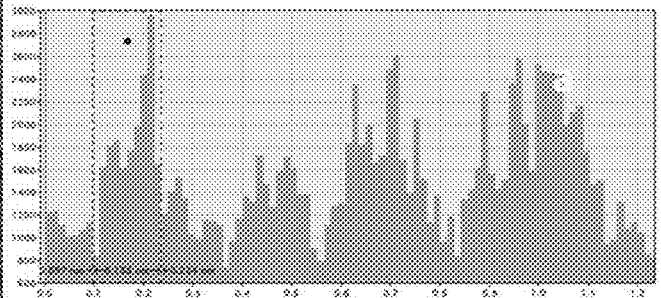
Figure 2C:
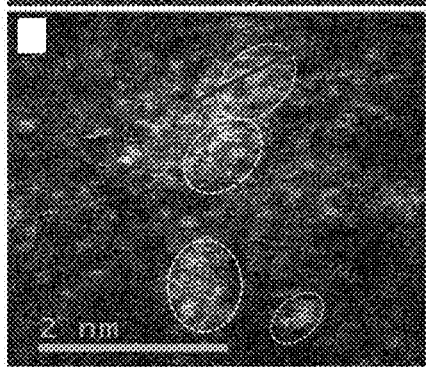
Figure 2D:
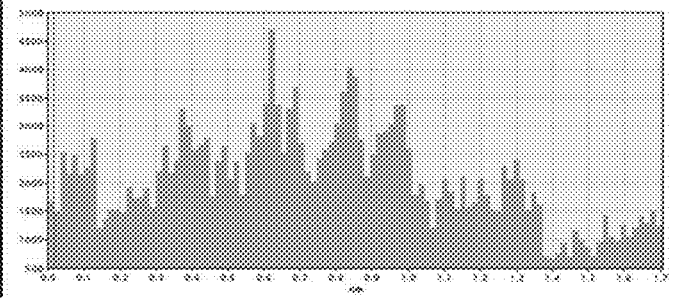
Figure 3:
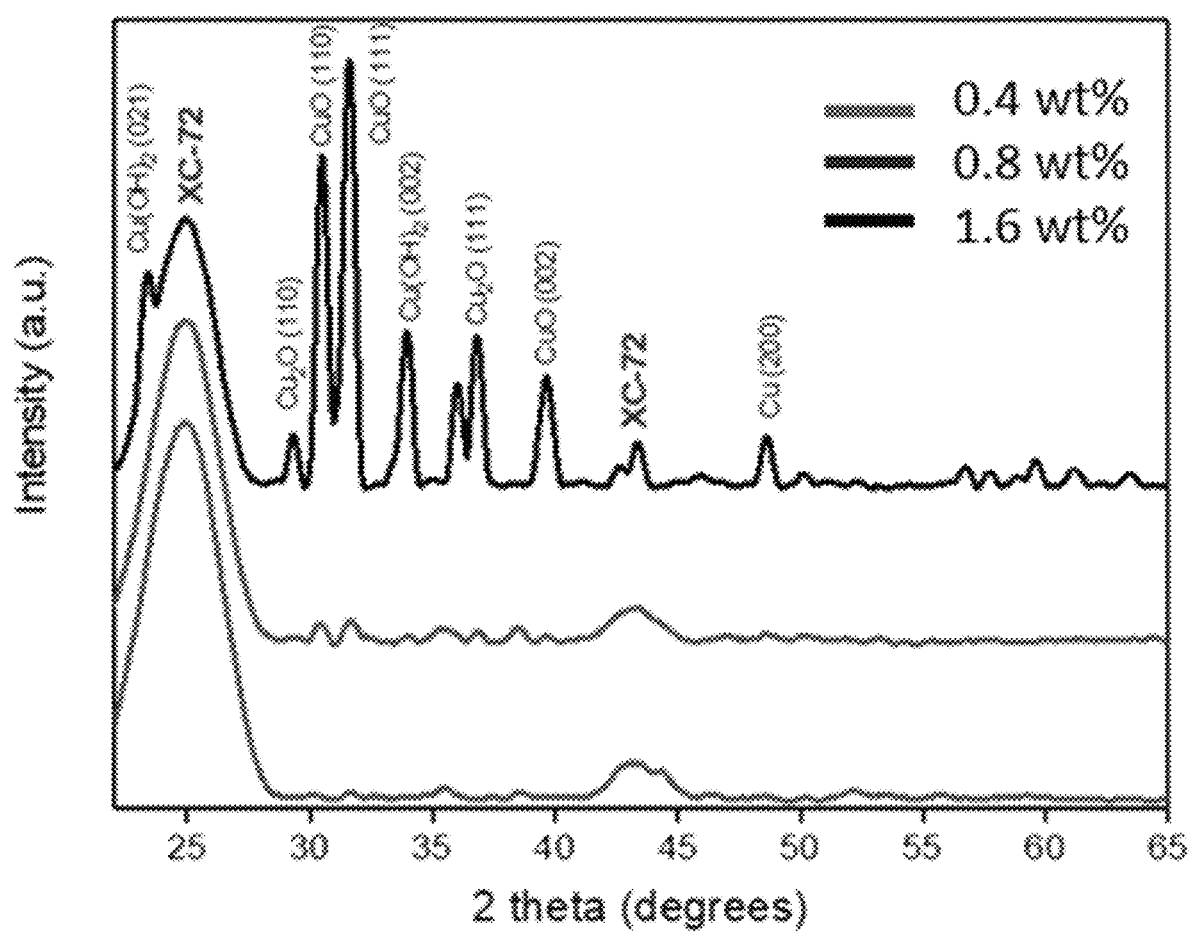
FIG. 3 shows the XRD pattern and that no significant diffraction peaks were detected for 0.4 wt. % and 0.8 wt. % Cu-on-C samples (the broad peak at 25° and 43° are due to the XC-72 carbon support), indicating that there is no lattice structure in Cu single atoms or these ultra-small clusters. As the Cu loading increases to 1.6 wt %, the diffraction peaks can be ascribed to metallic Cu, CuO, $Cu(OH)_2$ and $Cu_2O$ phases.

To gain further information on the structure of Cu in the catalyst, samples were measured using Powder X-ray diffraction. (XRD) and atomic resolution high-angle annular dark-field (HAADF) images through sub-Angstrom resolution, aberration-corrected scanning transmission electron microscopy (STEM) combined with Energy-dispersive EDX. XRD patterns in FIG. 3 show a visible broad spectrum pattern at 25°, only indicating XC-72 peaks in the 0.4 wt. %. However, no significant peaks were corresponding to crystalline Cu in the samples of 0.4 wt. % and 0.8 wt. %, which indicate the Cu single atoms or ultra-small clusters were formed completely in the sample. When the Cu loading mass increase to 1.6 wt. %, the presence of crystalline Cu phase became visible. All the distinguishable reflections corresponded to CuO, Cu(OH)$_2$, and Cu$_2$O phases, which had low intensity in lower loading sample. STEM images in FIGS. 2A and 2C show that no obvious nanoclusters and nanoparticles were observed. Individual Cu atoms can be discerned in the atomic resolution HAADF-STEM. FIGS. 2B and 2D show the intensity profile of a single atomic column. HAADF-STEM images of Cu single atom are revealed as bright spots marked with the circles, which existed predominantly highly dispersed isolated Cu single atoms. Neither sub-nanometer clusters nor nanoparticles were detected.

Figure 4:
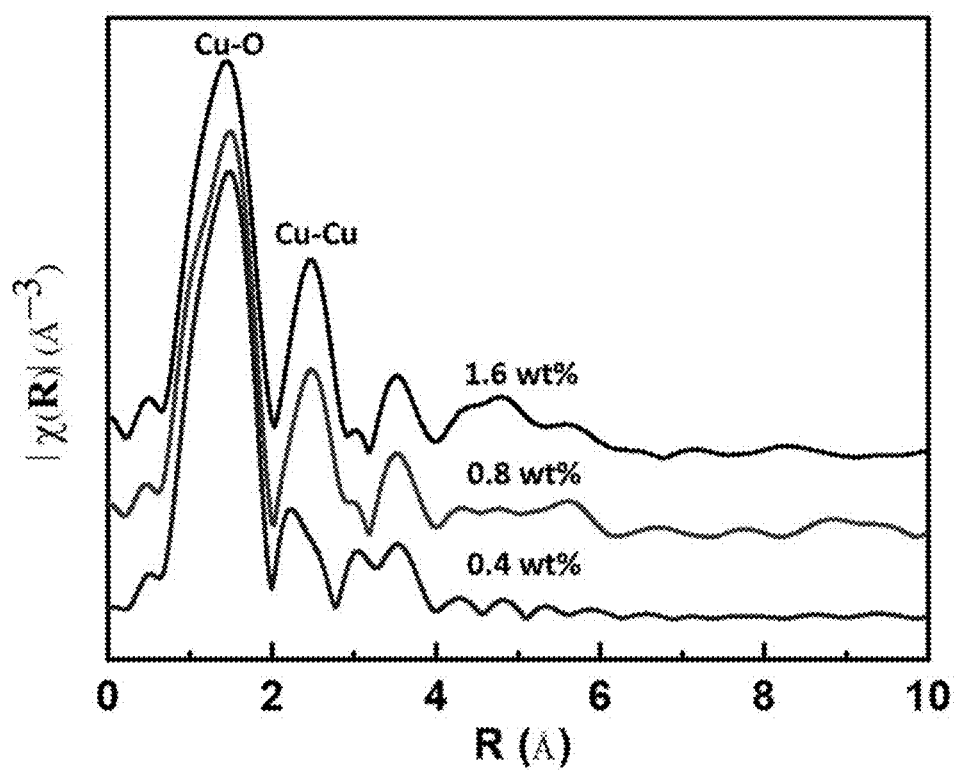
FIG. 4 shows the total EXAFS functions with $k_2$-weight in R-space extracted from the X-ray absorption spectra for all the specimens. There is only one prominent peak focused around 1.5 Å from the Cu—O shell with the coordination number 3.1, which is an indication that only Cu single atoms were synthesized for 0.4 wt. % Cu-on-C. But Cu—Cu characteristic distances approximately 2.7 Å in R-space were detected for both 0.8 wt. % and 1.6% Cu-on-C samples. It indicates that the samples also contain some clusters, in addition to single Cu atoms when the loading exceeds 0.8 wt. %.
Figure 5:
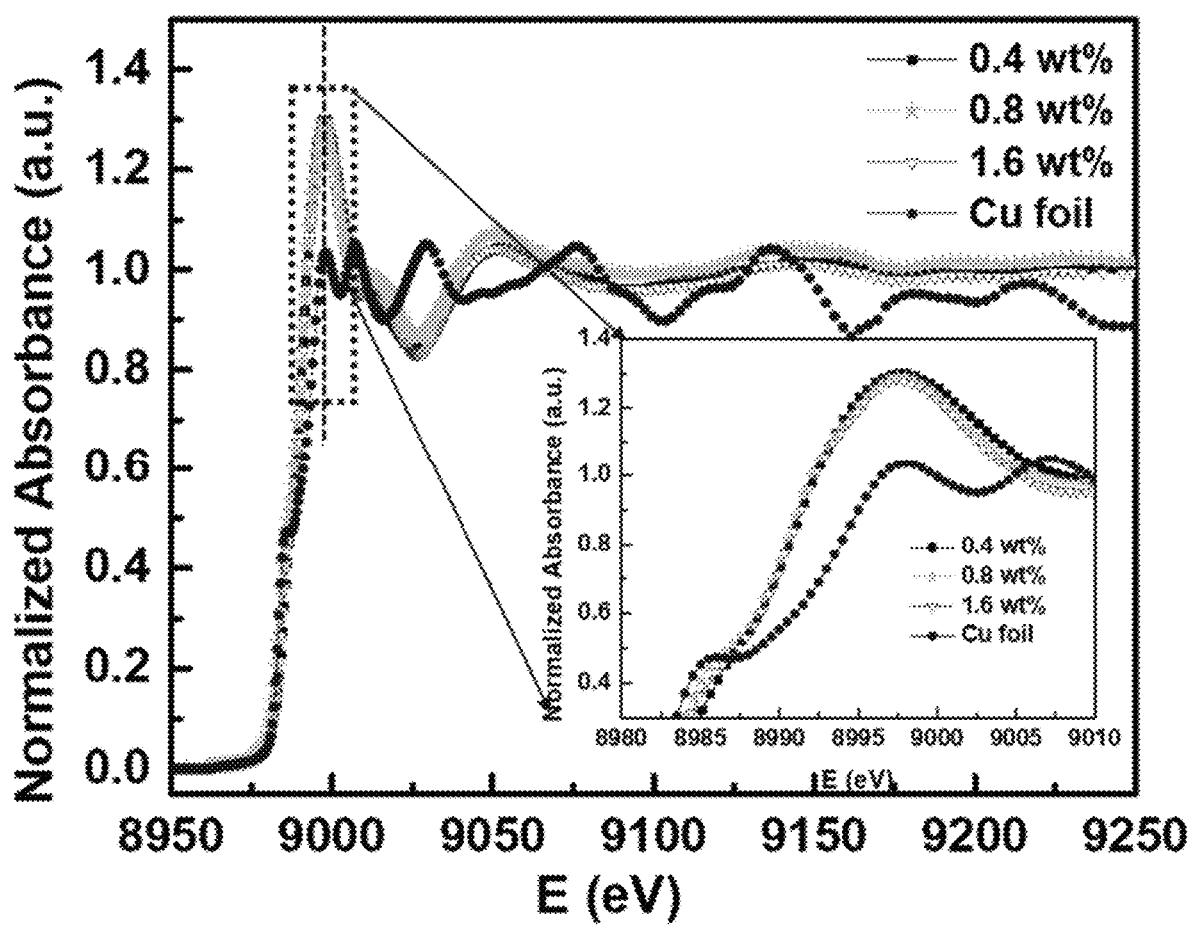
FIG. 5 shows the Cu K-edge XANES spectra of the 0.4 wt. %, 0.8 wt. %, and 1.6 wt. % Cu-on-C samples with reference samples (copper foil). Cu species with higher oxidation states for the prepared samples have stronger white-line adsorption features than Cu foil. The white-line intensity increased steadily with a decrease of Cu loading on carbon, suggesting the Cu become more positively charged with lower Cu loading (FIG. 5 and insert).
Figures 6A, 6B, 6C:
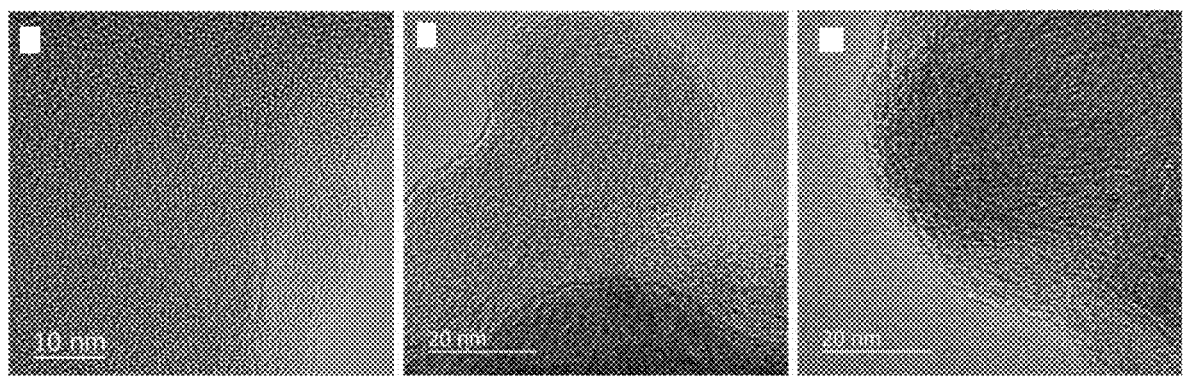
FIGS. 6A-6C show the HRTEM image of Cu-on-C samples.

To further investigate the changes in the structure of the oxide layer and gain insight into the chemical state of the active Cu species, XANES and EXAFS were used. FIG. 5 shows the Cu K-edge XANES spectra of the 0.4 wt. %, 0.8 wt. %, and 1.6 wt. % samples with standard samples. The XANES spectrum of the as-prepared Cu loaded on carbon show the features of Cu$_2$O and CuO in particular, the prominent shoulder at the edge marked with a dashed line at ~8982 eV and ~8992 eV. The metallic Cu in the initial sample is not shown in the XANES data. The lack of long-range order was further corroborated by EXAFS analysis (FIG. 4). Fitting a first coordination shell for Cu—O gave an average coordination number (CN) of 3.1 (table 2).

TABLE 2 shows that fitting a first coordination shell for Cu-O gave an average coordination number (CN) ranging from 3.22 to 2.88, as the loading increases from 0.4 wt.% to 1.6 wt.%.

| Edge | Sample Name | Paths | Bond Length R (ang) | Coordination Number (n) | Debye-Waller Factor (ang2) | Energy Shift ΔE (eV) | R-Factor |
|---|---|---|---|---|---|---|---|
| Cu K-edge | 0.4 wt % Cu-on-carbon | Cu—O | 1.930 ± 0.023 | 3.224 ± 0.660 | 0.0058 | 0.776 ± 0.660 | 0.0009 |
| | 0.4 wt % Cu-on-carbon | Cu—O | 1.956 ± 0.006 | 3.058 ± 0.575 | 0.00538 | 1.0314 ± 8.48 | 0.00096 |
| $S_0^2 =$ 0.9 | 0.4 wt % Cu-on-carbon | Cu—O | 1.948 ± 0.008 | 2.884 ± 0.736 | 0.00453 | 0.323 ± 8.350 | 0.00136 |

The electro-catalytic activity of the catalyst was probed by Linear sweep voltammetry (LSV) and cyclic voltammetry (CV) in 0.1M KHCO$_3$ solution. As shown by the example in FIGS. 7A and 7B for 0.8 wt. % Cu-on-C, they displayed obvious activity toward CO$_2$ reduction in the potential range from 0 V to −1.3 V versus RHE.

Electro-catalytic durability was tested through chronoamperometry at stable potentials between −0.5V and −1.3V for 6000 seconds. This allowed us to elucidate optimal potentials for catalytic selectivity and FE. FIG. 7F shows a representative current density and Faradaic efficiency of the CRR over 0.8 wt. % Cu loaded on carbon.

Figure 7D:
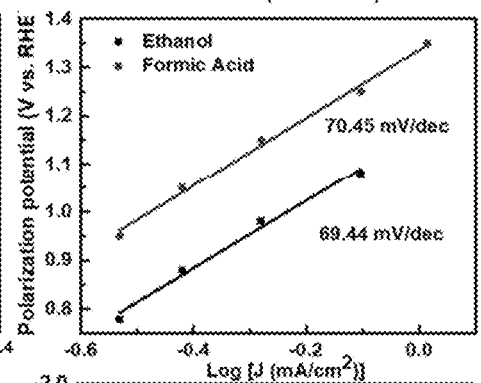
FIG. 7D shows the Tafel slope plots of overpotential versus current density for ethanol and formic acid. The Tafel slops are 69.44 mV/decade for ethanol and 70.45 mV/decade for formic acid, respectively.

To gain kinetic insight into CO$_2$ electro-reduction, Tafel plots of products of Cu single atoms were derived from the current density measured at different potentials, as is shown by the example in FIG. 7D. Production of ethanol was seen to be most favorable at 0.8 wt. % catalyst, exhibiting a Tafel slope of 69.44 mV/decade. The rate determining step was evaluated to be hydrogen diffusion to the attached species (59 mV/dec) with mild interactions of side reactions occurring.

Figure 7E:
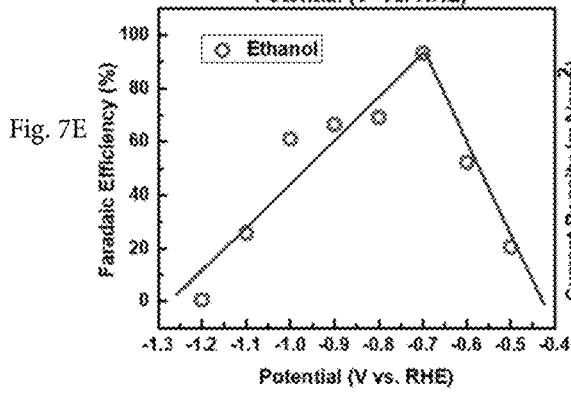
FIG. 7E shows the dependence of Faradaic efficiency as the function of polarization potential.
Figure 7F:
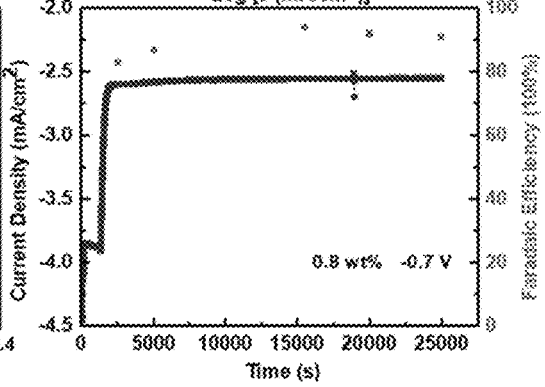
FIG. 7F shows an 8-hour stability test at constant voltage of −0.7V over 0.8 wt % Cu-on-C. The catalyst has been able to maintain FE of ethanol at ~85% or above at constant current during the run.
Figure 8:
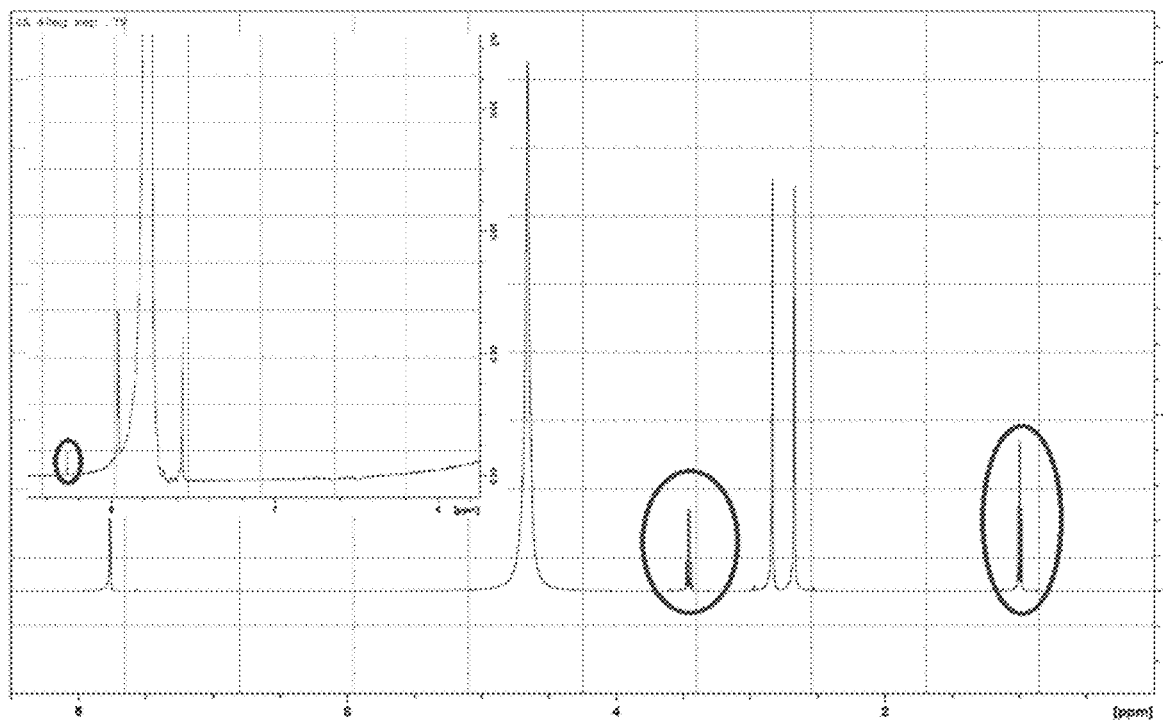
FIG. 8 shows NMR spectrum of ethanol generated from electro-catalysis over 0.8 wt. % Cu-on-C at −0.7V vs. RHE in $CO_2$ saturated bicarbonate solution. Features shown at 1.0 ppm and 3.45 ppm marked by the circles are $CH_3$ and $CH_2$ peaks of ethanol. The inset showing the presence of small amounts of formic acid.

FIG. 7E shows a peak performance of FE for 0.8 wt. % Cu loaded on carbon at different overpotential which indicated the high selectivity of ethanol products. Durability measurements were taken at −0.7V to account for the prominent evolved species. FIG. 7F). The catalyst exhibited a deviation of current density within 5% over the course of eight hours while no appreciable decrease in their relative Faradaic efficiency.

FIGS. 9A-9D display different 0.4 wt. % Cu loaded on carbon as catalysts for CRR, exhibiting 92.6% Faradaic efficiency. However, as can be seen from FIG. 10A, the 1.6 wt. % sample exhibited low selectivity for ethanol, reaching only a maximum of 38.8%.

Example 2

As-prepared inks, consisting of 5 mg of catalyst and prepared according to examples 1 and 2 (Cu and Rh at different loading concentrations), were mixed with 50 mg of Nafion® and 200 mg of methanol. The resulting solution was sonicated for 60 minutes to ensure full dispersion of the electro-catalyst and deposited in 5 uL droplets onto the rotating round disk electrode (RRDE) glassy carbon up to 20 uL. The RRDE glassy carbon had a surface area of 0.196 $cm^2$. The catalyst was tested at RDE rotation rate of 1600 rpm under $CO_2$ bicarbonate solution (pH 6.8) using an initial sweep rate of 100 mV/s from 0 to −1.3V versus RHE to ensure the full range of carbon dioxide reduction activity was realized. Sweep rates were increased at 50 mV intervals up to 300 mV/s to evaluate kinetic effects. Chronoamperometry was employed at −0.4V to −1.3V at 0.1V intervals to ensure both the stability of the catalyst and the resulting hydrocarbons and $CO/H_2$ formation was fully realized.

Example 3

Rhodium-on-carbon was synthesized in the same manner as example 1, using 0.034 wt. % rhodium as well as 0.68 wt, % Rh. The resulting catalyst exhibited the same single atom structures as well as loading dependent selectivity. The selectivity and Faradaic efficiency differed from that of Cu based materials described herein, with a high selectivity towards acetone production at 0.04 wt. % Rh (FIG. 12A). The kinetics detected showed the presence of side reactions, as indicated by a Tafel slope of 196 mV/decade.

As used herein, the singular forms "a", "an," and "the" include plural referents unless the context clearly dictates otherwise. Thus, for example, the term "a member" is intended to mean a single member or a combination of members and "a material" is intended to mean one or more materials or a combination thereof. As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary," as used herein to describe various embodiments, is intended to indicate that such embodiments are possible examples, representations, and/or illustrations of possible embodiments (and such term is not intended to connote that such embodiments are necessarily extraordinary or superlative examples).

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The invention claimed is:

1. A method of synthesizing a catalyst comprising:
adding a catalytic metal in its metallic form to molten alkaline metal;
atomically dispersing the catalytic metal in the molten alkaline metal;
forming an alkaline metal-catalytic metal solid;
converting a portion of alkaline metal in the alkaline metal-catalytic metal solid to alkaline metal hydroxide forming a metal-alkaline metal hydroxide solid;
mixing said metal-alkaline metal hydroxide solid with a conductive support material to form a mixture, the conductive support material being carbonaceous with a porous network and having catalytic metal decorated throughout the porous network;
removing alkaline metal hydroxide from the mixture leaving a mixture of metal in the conductive support material; and
drying the mixture of metal and the conductive support material to produce the catalyst containing the catalytic metal atomically dispersed over the conductive support material.

2. The method of claim 1, wherein the molten alkaline metal is lithium.

3. The method of claim 2, wherein converting the portion of the lithium-catalytic metal to metal-lithium hydroxide solid comprises reacting lithium in the metal-lithium solid with moist air.

4. The method of claim 2, further comprising mixing the metal-lithium hydroxide solid with the conductive support material using a mechanical method.

5. The method of claim 2, wherein the catalytic metal before adding to molten lithium is in metallic state and in the form of powder, ingot, wire and shredded pieces.

6. The method of claim 2, wherein the catalytic metal is a transition metal.

7. The method of claim 2, wherein the catalytic metal is a platinum group metal.

8. The method of claim 2, wherein the catalytic metal is dispersed in a single atom form.

9. The method of claim 1, wherein removing the metal hydroxide comprises washing the alkaline metal hydroxide with water thereby removing lithium.

10. The method of claim 9, wherein the washing comprises forming an alkaline water solution and modifying the carbonaceous support with oxygenated species serving as anchoring sites for the catalytic metal.

11. The method of claim 1 having a catalytic selectivity of at least 95% and Faradaic efficiency of at least 93% in converting of carbon dioxide to ethanol.

12. The method of claim 1 having a catalytic selectivity of about 100% and Faradaic efficiency of higher than 97% in converting carbon dioxide to acetone.

13. The method of claim 1, wherein the catalytic metal is a bimetallic compound.

14. The method of claim 1, wherein the catalytic metal is selected from the group consisting of copper and rhenium.

15. A method of synthesizing a catalyst comprising:
   forming an dispersion of multiple metals in a molten alkaline metal;
   forming an alkaline metal-multiple metal solid;
   converting a portion of alkaline metal in the alkaline metal-first catalytic metal-second catalytic metal solid to an alkaline metal hydroxide forming an alkaline metal hydroxide-multiple metal solid;
   mixing said alkaline metal hydroxide-multiple metal solid with a conductive support material;
   removing alkaline metal hydroxide from the mixture of the alkaline metal hydroxide-multiple metal solid and a conductive support material; and
   drying the multiple metal and conductive support mixture to produce the catalyst containing the multiple metals atomically dispersed over the conductive support.

16. The method of claim 15, wherein forming the dispersion of multiple metals comprises:
   adding a first catalytic metal in its metallic form to the molten alkaline metal; and
   adding a second catalytic metal in its metallic form to the molten alkaline metal.

17. The method of claim 15, wherein forming the dispersion of multiple metals comprises adding a multi-metallic catalytic compound to the molten alkaline metal.

18. The method of claim 15, wherein the conductive support material is a carbonaceous material having porous network and further catalytic metal is decorated through the porous network of carbonaceous material.

19. The method of claim 15, wherein removing the metal hydroxide comprises forming an alkaline water solution and modifying the conductive support material with oxygenated species serving as anchoring sites for the catalytic metal.

20. A method of synthesizing a catalyst comprising:
   adding a catalytic metal in its metallic form to molten alkaline metal;
   atomically dispersing the catalytic metal in the molten alkaline metal;
   forming an alkaline metal-catalytic metal solid;
   converting a portion of alkaline metal in the alkaline metal-catalytic metal solid to alkaline metal hydroxide forming a metal-alkaline metal hydroxide solid;
   mixing said metal-alkaline metal hydroxide solid with a carbonaceous conductive support material to form a mixture;
   removing alkaline metal hydroxide from the mixture leaving a mixture of metal in the conductive support material; and
   drying the mixture of metal and the conductive support material to produce the catalyst containing the catalytic metal atomically dispersed over the conductive support material.

\* \* \* \* \*